(12) United States Patent
Meinhold et al.

(10) Patent No.: US 7,699,869 B2
(45) Date of Patent: Apr. 20, 2010

(54) DEVICE FOR THE REMOVAL OF TICKS

(76) Inventors: Matthias Meinhold, Kilianstrasse 11, Nurnberg (DE) 90425; Hermann Kuffner, Am Rother Steig 11, Schwabach (DE) 91126

( * ) Notice: Subject to any disclaimer, the term of this patent is extended or adjusted under 35 U.S.C. 154(b) by 121 days.

(21) Appl. No.: 10/567,632

(22) PCT Filed: Aug. 3, 2004

(86) PCT No.: PCT/EP2004/008696

§ 371 (c)(1),
(2), (4) Date: Aug. 16, 2006

(87) PCT Pub. No.: WO2005/013837

PCT Pub. Date: Feb. 17, 2005

(65) Prior Publication Data

US 2007/0185528 A1     Aug. 9, 2007

(30) Foreign Application Priority Data

Aug. 9, 2003   (DE) ................................ 103 37 023
Jun. 30, 2004  (DE) ........................ 10 2004 031 682

(51) Int. Cl.
*A61B 17/50* (2006.01)
(52) U.S. Cl. ..................................................... 606/210
(58) Field of Classification Search ................ 606/131, 606/210, 205–207
See application file for complete search history.

(56) References Cited

U.S. PATENT DOCUMENTS 4,213,460 A * 7/1980 Weiner ........................ 606/131
4,976,718 A * 12/1990 Daniell ........................ 606/131
5,078,729 A * 1/1992 Eichhorn ..................... 606/210
5,282,806 A * 2/1994 Haber et al. ................. 606/139
5,407,243 A * 4/1995 Riemann ..................... 294/100

FOREIGN PATENT DOCUMENTS

| CH | 255260 A    | 6/1948  |
| DE | 297 19 008 U | 2/1998  |
| DE | 198 27 651 C1 | 1/2000  |
| DE | 198 60 172 A | 4/2000  |
| DE | 199 18 826 A1 | 10/2000 |
| DE | 200 12 032 U1 | 11/2000 |
| DE | 200 09 056 U | 12/2000 |
| DE | 100 23 740 A | 11/2002 |
| DE | 101 48 742 A | 6/2003  |

OTHER PUBLICATIONS

International Search Report, together with Written Opinion, corresponding to PCT/EP04/008696, under date of mailing of Nov. 29, 2004.

* cited by examiner

*Primary Examiner*—(Jackie) Tan-Uyen T. Ho
*Assistant Examiner*—Gregory Anderson
(74) *Attorney, Agent, or Firm*—Nancy J. Flint, Esq.

(57) ABSTRACT

The invention relates to a device, in particular, for the removal of parasites or ticks from the skin of animals or humans, comprises a housing, a spreading gripping tool, a spreading device, for spreading the gripping tool and a rotation device, for rotating the gripping tool about the axis of the device, whereby the gripping tool encloses a sealed cavity in the unspread state thereof for enclosing the parasite or the tick. The gripper tool is particularly made from an elastic or flexible material.

19 Claims, 5 Drawing Sheets

DEVICE FOR THE REMOVAL OF TICKS

This invention relates to a device for the removal of parasites or ticks from the skin of a host as described in the introduction to Claim 1.

Illnesses, in particular in human beings, as a result of a tick bite are spreading at an alarming rate. The prompt and correct removal of the tick from the skin of the host is simultaneously prevention and therapy, whereby the term "correct removal" as used in this document means the extraction of the undamaged tick from the host without squashing or otherwise irritating the tick, which is what initially causes the infection.

Conventional methods for the removal of ticks from human skin result in the squashing of the tick when the tick is firmly grasped and removed. In particular with parasites that contain infectious substances, this type of removal results in the expulsion of infectious material and thereby initially causes the illness. The most important objective, in addition to the prevention of exposure, however, is the gentle removal of the intact parasite.

Figure 1:
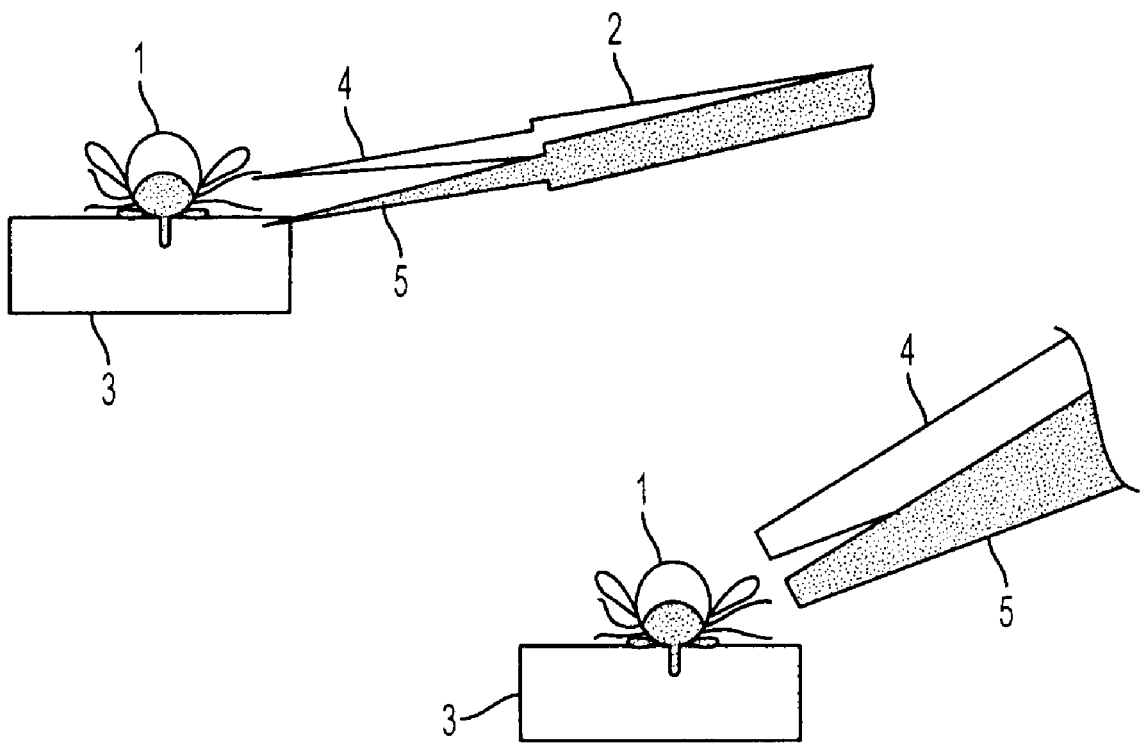

Conventionally, ticks are removed using tongs or forceps. It is thereby impossible to prevent the squashing of the tick or parts of the tick. As a result of the use of a cord, this risk can be reduced to some extent when the equipment is used correctly, although this method is tedious, time-consuming and not always successful. In difficult parts of the body such as the armpit, for example, the ability to employ the method that uses a cord is severely limited In the accompanying drawings that illustrate the process of removing a tick by means of forceps, for purposes of clarity, the relative sizes of the forceps, fingernail or extractor to the tick are frequently distorted. The drawings may therefore give the impression that the tick is simply grabbed by the head and then removed. In fact, however, the tip of the forceps is generally several times larger than the tick itself, as a result of which the body of the tick is inevitably squashed, which results in the discharge of potentially infectious contents of the tick's stomach and intestine. This situation is illustrated in FIG. 1, whereby the upper portion of FIG. 1 shows the frequently illustrated but distorted relative sizes of the forceps and the tick, while the lower portion of FIG. 1 shows the correct size ratio, from which it is apparent that the tick is essentially squashed as a result of the large size of the arms of the forceps.

If the recommendations that are to be found in the medical literature or on the Internet are followed, the use of pointed forceps, a tick remover, a cord or a fingernail can be used for the correct removal of a tick. Although removal using a cord is gentle on the tick and therefore on the patient, it is a time-consuming process and cannot be performed on some parts of the body, the use of rigid or relatively inflexible forceps, including the fingernail, inevitably results in the squashing of the tick's body and thus an increased risk of infection, as discussed above.

DE 19860172 A1 also describes an automatic tick remover. This device has a gripper device which can be opened and closed as desired via a gripper sleeve, and is used to grasp a tick. The tick remover is also provided with a rotation drive mechanism with which the gripper device can be driven in rotation. There is also a linear drive device that is formed by a compression spring, by means of which the gripper device can be moved in a linear direction away from the skin of the host organism. The coordination of the rotational movement and the linear extraction movement of the gripper device is controlled by a control device that includes a trigger finger and a support finger, for example, or a snap-in pin and a releasing bar, which is activated by the rotational movement of the gripper device for the release of the snap-in pin. The extraction of a tick is therefore done automatically in a few seconds. In the device of the prior art, of course, the gripper and rotation mechanism are coupled with each other, although the grippers are rigid, which means that the infectious material can be discharged into the host organism.

DE 19827651C1 shows a device that has gripper arms for the removal of ticks, whereby said arms are connected to one another in a single piece by means of a support web at a point between two gripper pieces and gripper jaws that project out of a housing. The inner ends of the gripper arms are supported on diagonal surfaces in the housing. On account of the inherent elasticity of the gripper arms, which are molded in one piece from elastic plastic, the gripper jaws are pressed together at a specified closing force when the device is not actuated. Although the device of the prior art for the removal of ticks operates with plastic forceps, it poses a risk that the two sharp-pointed grippers will squash the tick.

The object of the invention is to create a device of the type described above that makes possible the correct removal of a tick or a similar parasite from the host.

The invention teaches that this object can be accomplished by a device for the removal of parasites or ticks that has the characteristics disclosed in Claim 1. Preferred realizations of the invention are disclosed in the subclaims.

The device claimed by the invention, which is used in particular for the removal of parasites or ticks from the skin of animals and humans and is also called a tick remover, comprises a housing, a spreadable gripper tool, a spreader device for the spreading of the gripper tool and a rotation device for the rotation of the gripper tool around the axis of the device, whereby the gripper tool in its un-spread state encloses an essentially closed cavity that is designed to receive and contain the parasite or of the tick. In other words, the cavity realized in the interior of the gripper tool is essentially completely enclosed by the gripper tool in the closed position.

The device preferably also has a presser device that acts in the axial direction of the device for the actuation of the spreader device and the rotation device of the gripper tool. A first actuation of the presser device thereby effects a spreading of the gripper tool via the spreader device and a second actuation of the presser device effects a rotation of the gripper tool. A closing of the gripper tool is also effected by the first or second actuation of the presser device.

In a first preferred embodiment, the first actuation of the presser device effects a movement in the axial direction into the device and the second actuation in the axial direction after the first actuation effects a movement out of the device. In other words, in the preferred embodiment, which is similar in shape to a mechanical pencil, the presser device is actuated by means of a press pin and when the press pin is pushed in, the gripper tool is spread. When the press pin is released, i.e. actuated in the direction opposite to the first actuation, the gripper tool is rotated. The closing of the gripper tool can take place either at the end of the first actuation or at the beginning of the second actuation of the press pin.

In a second preferred embodiment, the first actuation of the presser device in the axial direction also effects a movement into the device, and the second actuation that follows the first actuation also effects a movement in the axial direction into the device. In other words, when the device is realized in a form similar to a mechanical pencil, the spreading is effected by a first pressing of the press pin. The closing of the gripper tool can in this case also occur at the end of the first actuation or at the beginning of the second actuation.

The gripper tool is preferably formed from two or more segments, whereby particular preference is given to a gripper tool that is formed from two, three or four segments. The segments of the gripper tool are preferably realized so that they are elastic.

The cavity of the gripper tool can be formed by making the segments of the gripper tool taper toward the tip of the gripper tool and by gripper jaws that face inward. The segments of the gripper tool also preferably have a spring force, against which the spreading of the segments takes place. In other words, the segments are realized so that on account of their inherent spring force, when they are closed they form the interior cavity and completely enclose it, and so that the spreading of the segments, i.e. an opening of the gripper tool, takes place against the spring force of the segments.

The gripper tool can also be coated with an adhesive and/or be provided with barbs. The device can also have a suction device that is connected with the gripper tool. These additional measures can be used to improve the hold on the tick.

The gripper tool is preferably made of an elastic or flexible material such as silicon, in particular medical-grade silicon, or from a suitable elastic, plastic-coated material.

The device also preferably has a device to paralyze or kill the parasite. For example, this step can consist of the killing of the parasite by means of an electric current or laser beam, as well as the paralysis or killing of the parasite by means of a suitable drug.

The gripper tool is preferably disposable, so that for sanitary reasons the gripper tool can be discarded after it has been used once, to eliminate the risk of transmission of an infection by a gripper tool that has previously been used. In particular, the gripper tool is a unit that is separate from the rest of the mechanical portion of the device, and can be attached to the rotation device by means of a bayonet connector or similar connector. The result is a sanitary separation between the disposable gripper tool and the reusable mechanical portion of the tick remover. The gripper tool is also available in various sizes and material thicknesses that can be used interchangeably, so that a gripper tool that is appropriate to the size of the parasite can be used, which further reduces the risk of squashing the parasite.

The device preferably has an ejector device for the ejection of the gripper tool. It is thereby possible to separate the gripper tool from the device after the tick is inside the cavity of the gripper tool, or when a gripper tool of another size must be used. In particular, the ejector device can release the gripper tool from the device when the process of removing a parasite has been completed.

The rotation principle described above is based on the observation that the rotation of the tick itself or of the gripper tool on the tick's body causes the tick to detach from the host.

The tick remover is also designed so that it can be operated with one hand and can therefore also be used on "difficult" parts of the body, such as the armpit, for example.

The gripper tools are advantageously available in a plurality of sizes, so that they can be used to remove everything from the smallest nymphs to engorged adult ticks. Different material thicknesses are provided for use under different conditions on humans and animals. The gripper tool can also have a moisture dispenser so that the tick, which is conventionally caught alive by the gripper tool, can survive for some period of time in the detachable disposable gripper tool, so that it can be subjected to further testing if necessary.

Figure 2:
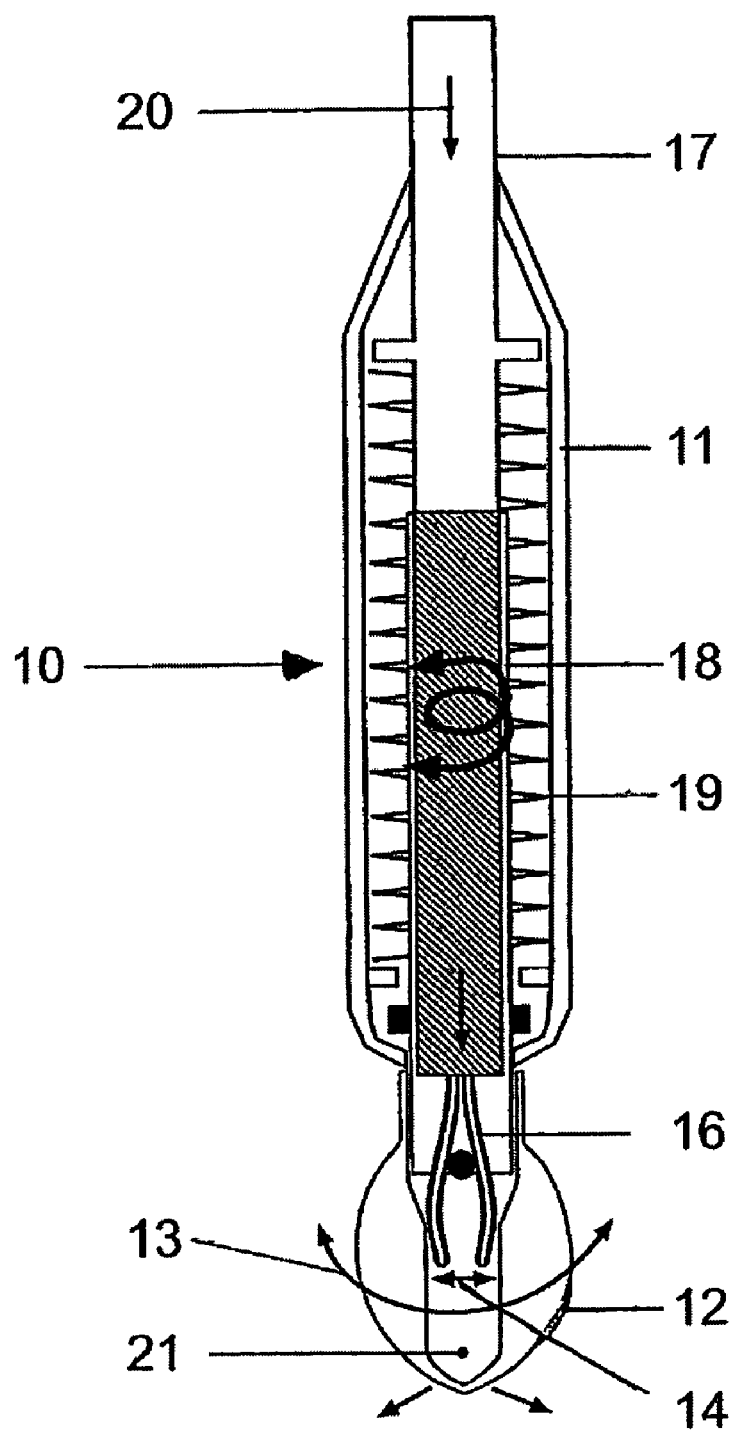
Figure 3:
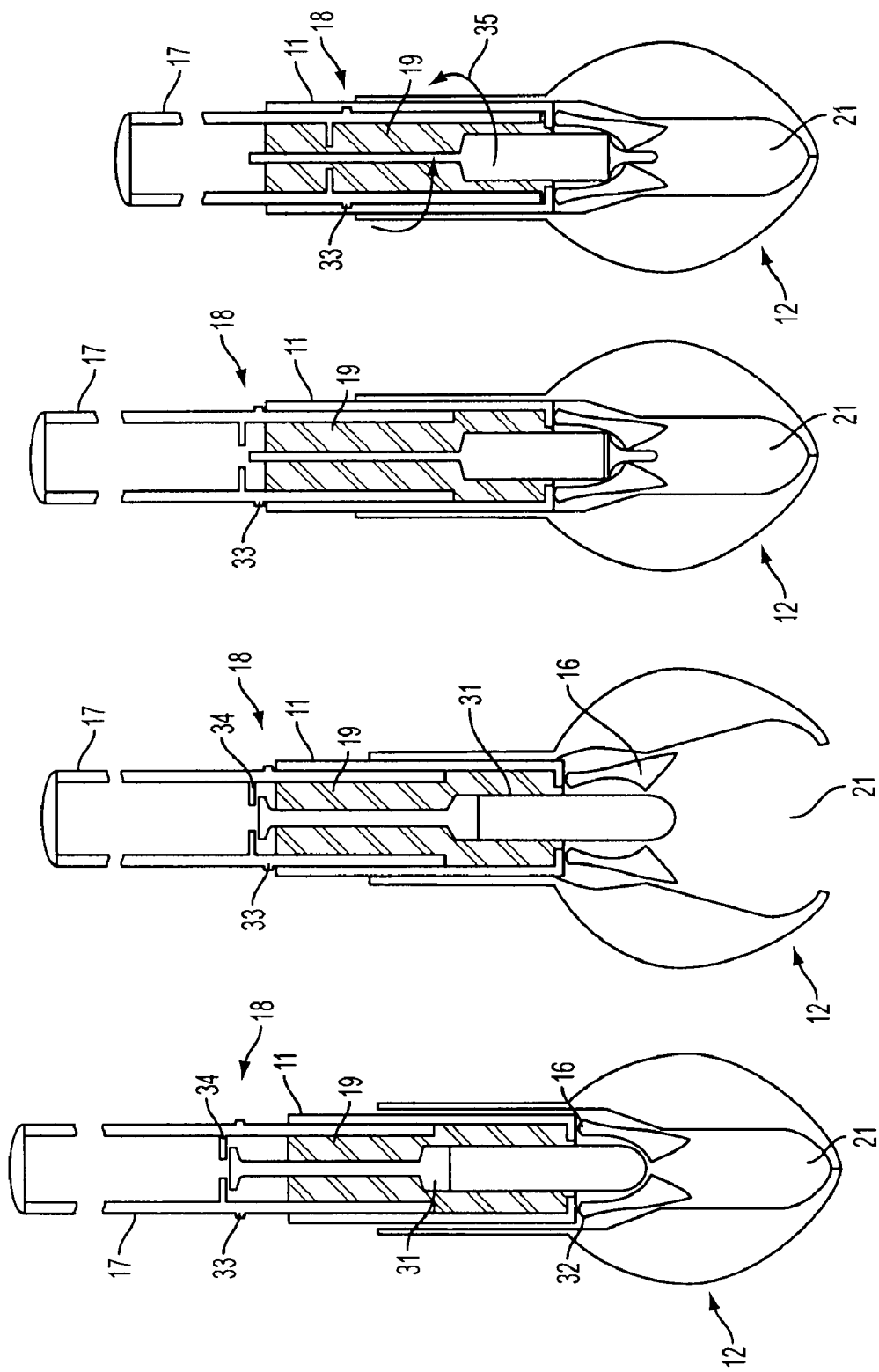
Figure 4:
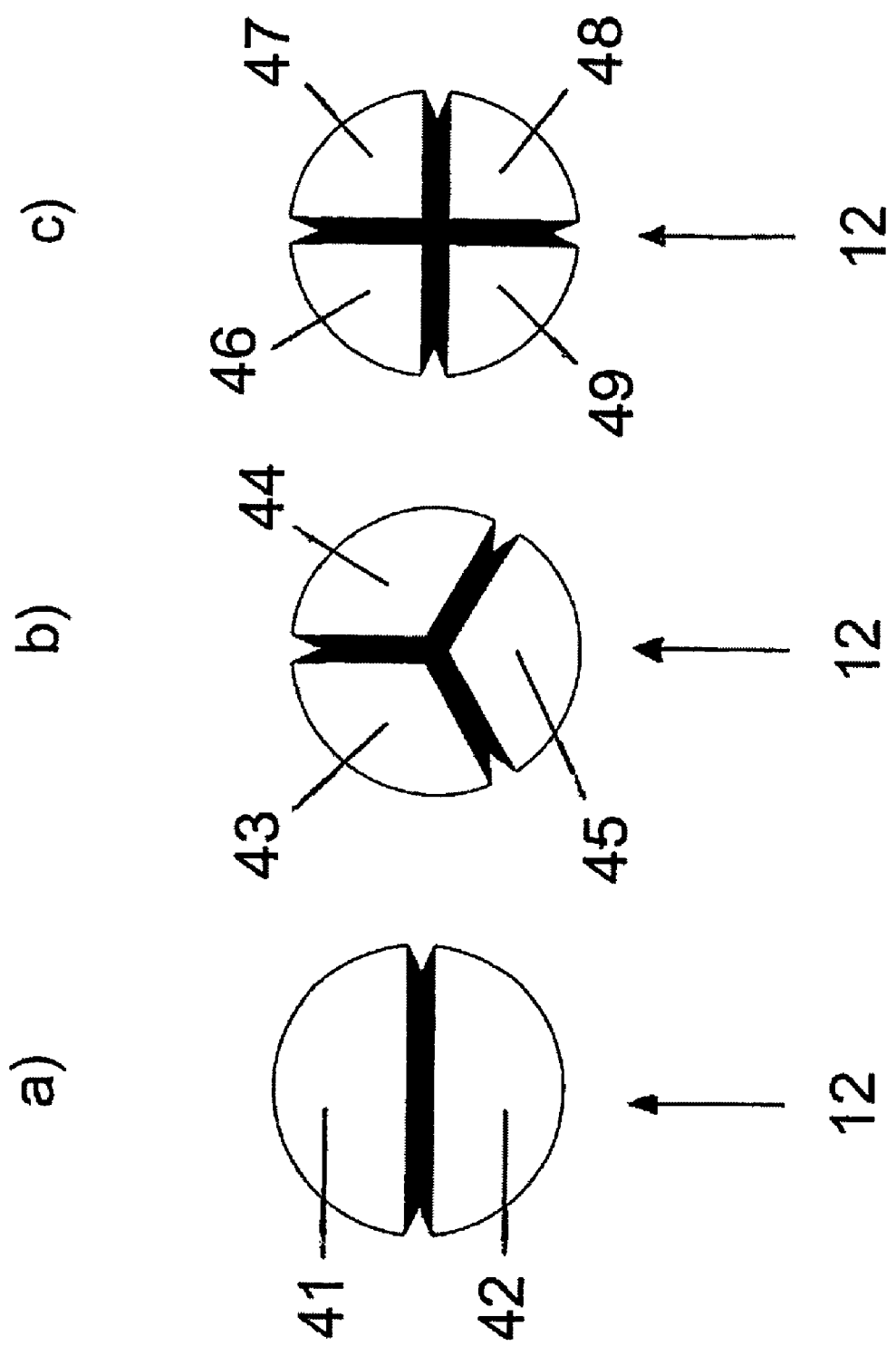
Figure 5:
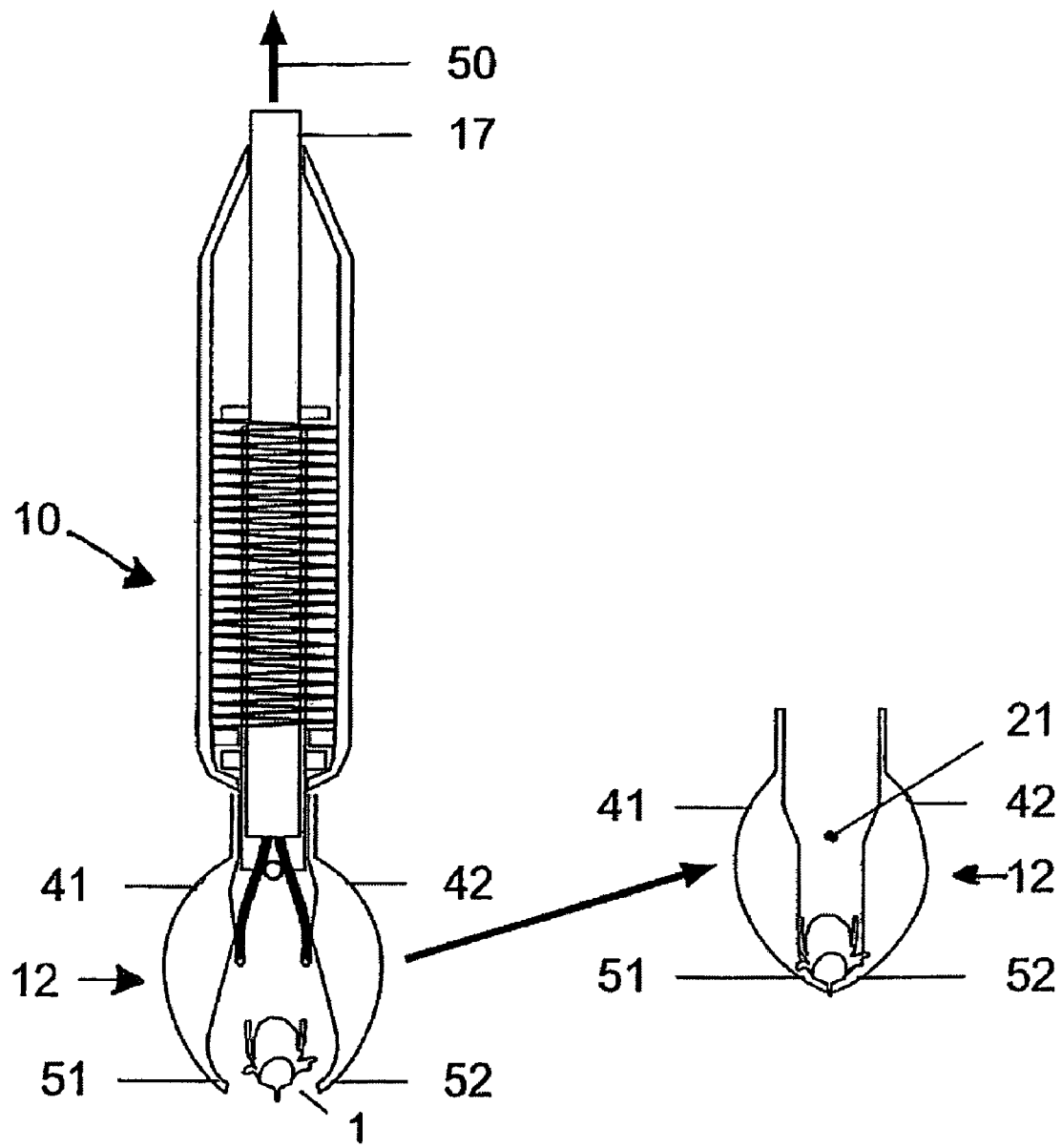

Preferred embodiments of the invention are illustrated in the accompanying drawings, in which:

FIG. 1 illustrates the distorted and real relationship between the relative sizes of a tick and forceps, FIG. 2 is a first exemplary embodiment of the device claimed by the invention, FIG. 3 is a second exemplary embodiment of the device claimed by the invention, FIG. 4 shows different segment variants of the gripper tool, and FIG. 5 illustrates the use of the first embodiment of the invention.

FIG. 1 has already been explained in the introductory portion of the description, and in its upper portion shows an illustration of the distorted size relationship between a tick 1, which has bored into the skin 3 of a host, and forceps 2 of the type that are described in the literature. The lower portion of FIG. 1, on the other hand, reflects the actual size relationship and clearly shows that the forceps arms 4, 5 are oversized in relation to the tick 1, as a result of which a squashing of the tick 1 during removal is inevitable.

FIG. 2 shows a first embodiment of the tick remover 10 claimed by the invention which has a pen-shaped housing 11, on the lower end of which there is a spreadable and rotatable gripper tool 12, as indicated by the arrows 13, 14 and 15. The arrow 13 thereby symbolizes the direction of rotation of the gripper tool around the longitudinal axis (not shown) of the device 10, the arrow 14 the spreader device for the spreading of the gripper tool 12 and arrow 15 the opening movement of the gripper tool 12. In the pen-shaped housing 11, there is a presser device that is realized in the direction of the longitudinal axis in the form of a press pin 17, which acts on a spreading device 16 to spread the gripper tool and a rotation device 18 for the rotation of the gripper tool. A spring element 19 which is located in the interior of the housing 11 provides the force necessary to make available the mode of operation of the tick remover 10 described below.

The tick remover 10 functions similar to a mechanical pencil. In such devices, applying pressure with the thumb spreads the gripper panels at the tip of the pencil to release the pencil lead.

In the first exemplary embodiment illustrated in FIG. 2, when thumb pressure is applied to the press pin 17 in the direction of the longitudinal axis into the interior of the housing, as symbolized by the arrow 20, and corresponds to a first actuation, the spreader device 16 opens a gripper tool 12 that is slotted on the tip, which can be in the form of a small silicon ball, for example. This gripper tool 12 is positioned over the tick and is pressed against the skin so that the tick is located in the opening of the gripper tool 12. As the thumb pressure on the press pin 17 is removed, i.e. as the press pin moves opposite to the direction of the arrow 20 which corresponds to a second actuation, the spreader device 16 moves backward and the gripper tool 12 encloses the tick in the cavity 21. The further removal of thumb pressure from the press pin effects a rotation of the gripper tool 12 by means of the rotation device 18, as a result of which the tick is detached from the skin and picked up by the gripper tool 12. This gripper tool 12 is detachably fastened to the device 10 and can be removed so that, if necessary, it can be sent along with the tick to a laboratory for testing. The use of a disposable gripper tool 12 is preferred for sanitary reasons.

FIG. 3 shows a second embodiment of the tick remover 30 claimed by the invention in a schematic illustration, whereby FIG. 3 shows the tick remover in four positions, A, B, C and D.

The second embodiment of the tick remover 30, like the first embodiment, is comparable to a mechanical pencil, whereby the tick remover 30 has a housing 11, a spreadable and rotatable gripper tool 12 and a press pin 17. The rotation and spreading devices of the gripper tool 12 and the gripper tool 12 of the second embodiment are the same as in the first embodiment, so that they do not need to be described again here. The second embodiment also has a rotation device 18 and a spring 19 to store energy and to make the necessary forces available.

In position 3A of the tick remover 30 in FIG. 3, which corresponds to the idle position, the gripper tool 12 is closed and completely encloses an interior cavity 21, the size of which is sufficient to securely hold the parasite. The stud 31 of the spreader device 16 is also in the idle position, and is located in a recess between appropriately shaped spreader jaws 32 for the spreading of the gripper tool 12.

Position 3B in FIG. 3 shows the tick remover 30 during or after a first actuation of the press pin, i.e. the press pin 17 is pressed inward along the longitudinal axis of the tick remover 30. As a result of the movement of the press pin 17 downward in FIG. 3, the transverse stud 31 of the spreader device 16 is also pushed downward by a driver 34 because of its guidance in a groove, which causes a spreading, i.e. opening, of the gripper tool 12 by the action of the stud 31 on the spreader jaws 32.

In position 3C of the tick remover 30, the pressure on the press pin is maintained in the same direction as in position 3B. This position can be considered as the terminal position of a first actuation or as the beginning of a second actuation, because in the second embodiment of the tick remover 30, there can be a seamless transition between the first and second actuations. On account of its guidance in a groove, the stud 31 is now rotated by 90.degree. around its longitudinal axis, whereupon, as a result of the configuration of the stud, i.e. the presence of the flattened portion shown in the drawing, the gripper 12 closes under its own spring force. Because the upper end of the stud 31 is also flattened, the stud now lies in the opening of the driver 34 of the press pin 17 and can therefore not be pushed any farther, i.e. the stud 31 has reached its terminal position.

Position 3D of the tick remover 30 is reached by the further actuation of the press pin 17 in the same direction along the longitudinal axis of the device 30. Further actuation in the same direction as the first actuation effects a twisting or rotation of the closed gripper tool 17, illustrated symbolically by the arrow 35. The rotation of the gripper tool 17 is effected by a rotation device 18 which is formed by two nubs 33 that are located on the outside of the press pin 17, and which are now engaged in the internal thread of the housing 11. As pressure continues to be exerted on the press pin 17, the housing 11 on which the gripper 12 is fastened is therefore rotated.

One advantage of the second embodiment is that the tick remover opens, closes and rotates the gripper tool by actuation or insertion of the press pin in one direction. The sequence of movement ends when the press pin is pushed in all the way. In contrast to the first embodiment 1, as a result of the unidirectional actuation of the press pin, the alternation or fluctuation of loads on the device is prevented, thereby eliminating any "trembling", in particular for the removal of extremely tiny ticks.

FIG. 4 shows variants of the gripper tool 12 in schematic views from overhead. Part a) of FIG. 4 shows a gripper tool consisting of two segments 41, 42, i.e. 180° sectors, Part b) shows a gripper tool consisting of three segments 43, 44, 45, i.e. 120° sectors, and Part c) shows a gripper tool consisting of four segments 46, 47, 48, 49, i.e. 90° sectors. For purposes of illustration, the various gripper tools are shown slightly open, to give an impression of the path followed by the interfaces. When the gripper is closed, the edges of the segments are in contact with one another.

FIG. 5 is a schematic illustration of the use of the first embodiment of the tick remover 10 with a gripper tool 12, consisting of two segments 41, 42 shown in schematic cross section along the longitudinal axis of the device 10, i.e. of the tick remover 10. The tick remover 10 in the open position of the gripper tool 12 is placed over the tick 1 on the skin of the host. By releasing the press pin 17 in the direction 50, the segments 41 and 42 are closed and a rotation of the gripper tool 12 is effected, as a result of which the tick is removed and lifted from the skin of the host. The tick 1 is then located in its entirety inside the closed cavity 12 of the gripper tool 12, as illustrated in the right-hand portion of FIG. 5. The cross section of the segments 41 and 42 of the gripper tool also shows that the thickness of the segment decreases toward the tip of the gripper tool, i.e. a segment 41, 42 tapers in thickness toward the tip of the segment. The segment jaws 51, 52 formed by the taper also point inward, on one hand to grasp the tick as close as possible to the host, and on the other hand to form the cavity 21 in the closed position. The illustration does not show that the tapering of the wall thickness of the segments toward the tip of the gripper tool is also present in the gripper tools that consist of more than two segments, as shown schematically in FIG. 4. An elastic or flexible material is also used for the gripper tool to prevent a squashing of the tick. The gripper tool can also be detachably connected with the rotation device, for example by means of a bayonet connection (not shown), so that the gripper tool can be removed after a single use. The gripper tool can also have a moisture dispenser (not shown), so that the tick can survive inside the gripper tool for some period of time if the gripper tool containing the living tick is to be sent for testing. In the simplest case, the moisture dispenser can be formed by the introduction of a drop of water into the gripper tool.

When the tick removal has been completed, i.e. when the living tick is in the cavity, the gripper tool 12 is detached from the rotation device of the tick remover by means of an ejector device (not shown), i.e. it is ejected. The ejected gripper tool with the tick inside it can then be sent for testing of the tick to determine its infectious status.

NOMENCLATURE

1 Tick
2 Forceps
3 Host skin
4 Forceps arm
5 Forceps arm
10 Tick remover
11 Housing
12 Gripper tool
13 Rotation device
14 Spreading device
15 Opening direction
16 Spreading direction
17 Press pin
18 Rotation device
19 Spring
20 Direction of the insertion of the press pin
21 Cavity
30 Tick remover
31 Stud
32 Spreading jaws
33 Nubs
34 Driver
35 Direction of rotation of gripper tool
41 180° segment
42 180° segment
43 120° segment
44 120° segment

45 120° segment
46 90° segment
47 90° segment
48 90° segment
49 90° segment
50 Direction of the outward motion of the press pin
51 Segment jaw
52 Segment jaw

The invention claimed is:

1. A device for the removal of parasites or ticks from the skin of animals and humans, comprising:
   a. a housing;
   b. a spreadable gripper tool;
   c. a spreader device, separate from the gripper tool, for spreading the gripper tool;
   d. a rotation device for the rotation of the gripper tool around the longitudinal axis of the device; and
   e. a presser device that is actuated in the axial direction of the device to actuate the spreader device and the rotation device of the gripper tool, wherein a first actuation of the presser device effects a spreading of the gripper tool by the spreading device and wherein a second actuation of the presser device effects a rotation of the gripper tool, wherein further the gripper tool in its un-spread position encloses an essentially closed cavity that is designed to contain the parasite or the tick.

2. The device as claimed in claim 1, wherein the gripper tool is detachably connected to the exterior of the rotation device.

3. The device as claimed in claim 1, wherein a closing of the gripper tool is effected by the first or second actuation of the presser device.

4. The device as claimed in claim 3, wherein the first actuation of the presser device takes place in the axial direction into the device and the second actuation that follows the first actuation takes place in the axial direction out of the device.

5. The device as claimed in claim 3, wherein the first actuation of the presser device takes place in the axial direction into the device and the second actuation that follows the first actuation continues in the axial direction into the device.

6. The device as claimed in claim 3, wherein the gripper tool is formed by two or more segments.

7. The device as claimed in claim 6, wherein the gripper tool is formed by two, three or four segments.

8. The device as claimed in claim 6, wherein the segments of the gripper tool are elastic.

9. The device as claimed in claim 8, wherein the segments of the gripper tool are tapered toward the tip of the gripper tool and form inward-facing gripper jaws.

10. The device as claimed in claim 9, wherein the segments of the gripper tool comprise a spring force, against which the spreading of the segments takes place.

11. The device as claimed in claim 3, wherein the gripper tool is coated with an adhesive.

12. The device as claimed in claim 3, wherein the gripper tool comprises barbs.

13. The device as claimed in claim 3, wherein the device comprises a suction device that is connected with the gripper tool.

14. The device as claimed in claim 3, wherein the device comprises an apparatus to paralyze or kill the parasite.

15. The device as claimed in claim 3, wherein the gripper tool is interchangeable and replaceable.

16. The device as claimed in claim 15, wherein the gripper tool comprises interchangeable different sizes and material thicknesses.

17. The device as claimed in claim 3, wherein the gripper tool comprises a moisture dispenser.

18. The device as claimed in claim 3 wherein the device further comprises an ejector device for the ejection of the gripper tool.

19. The device as claimed in claim 18, wherein the ejector device detaches the gripper tool from the device when the process of removing the parasite is completed.

* * * * *